United States Patent [19]

Sinkevitch

[11] 4,199,425
[45] Apr. 22, 1980

[54] SOLID ELECTROLYTE EXHAUST GAS SENSOR WITH INCREASED $NO_x$ SENSITIVITY

[75] Inventor: Robert M. Sinkevitch, Belle River, Canada

[73] Assignee: General Motors Corporation, Detroit, Mich.

[21] Appl. No.: 964,924

[22] Filed: Nov. 30, 1978

[51] Int. Cl.² ............................................. G01N 27/58
[52] U.S. Cl. .................................................. 204/195 S
[58] Field of Search ............. 204/195 S, 1 S; 324/29; 123/119 E; 60/276

[56] References Cited

U.S. PATENT DOCUMENTS

| 3,454,486 | 7/1969 | Davies | 204/195 S |
| 3,768,259 | 10/1973 | Carnahan et al. | 60/276 |
| 3,843,400 | 10/1974 | Radford et al. | 204/195 S X |
| 3,935,089 | 1/1976 | Togawa et al. | 204/195 S |
| 4,067,695 | 1/1977 | Miyaguchi | 23/254 E |
| 4,126,532 | 11/1978 | Takao et al. | 204/195 S |

*Primary Examiner*—G. L. Kaplan
*Attorney, Agent, or Firm*—Robert J. Wallace

[57] ABSTRACT

A solid electrolyte exhaust gas oxygen responsive sensor having a platinum exhaust gas electrode and a porous ceramic coating on the electrode. The porous ceramic coating contains rhodium for making the sensor also responsive to $NO_x$. In a specific example, rhodium permeates a gamma alumina porous overcoat on a sputtered platinum film serving as an exhaust gas electrode on a zirconia solid electrolyte member.

3 Claims, 2 Drawing Figures

SOLID ELECTROLYTE EXHAUST GAS SENSOR WITH INCREASED NO$_x$ SENSITIVITY

BACKGROUND OF THE INVENTION

This invention relates to a solid electrolyte oxygen responsive exhaust gas sensor. It more specifically relates to enhancing response of such a sensor to oxides of nitrogen.

Automotive catalysts designed for lowering emissions of hydrocarbons, carbon monoxide and oxides of nitrogen are referred to as three-way catalysts. Emission control systems employing such catalysts have been designated as Phase II emission systems. In such systems, best results are obtained when the exhaust gas stream is maintained at stoichiometry. The exhaust gas stream is at stoichiometry when all the oxidizing and reducing species therein are chemically balanced. Hydrocarbons, carbon monoxide and hydrogen are reducing species. Oxygen and oxides of nitrogen are oxidizing species. A concentration change in any of the species will offset exhaust gas chemical balance. The three-way catalytic converter performs best at exhaust gas stoichiometry, i.e. when all oxidizing and reducing species are balanced. I recognize that this should include nitrogen oxides as an oxidizing species as well as free oxygen. For example, to maintain stoichiometry, oxygen concentration should be lowered if oxides of nitrogen increase. Otherwise, the exhaust gas will be lean, and optimum conversion will not be obtained.

Solid electrolyte exhaust gas sensors are well known for monitoring exhaust gas stoichiometry, to regulate internal combustion engine air/fuel ratio at stoichiometry. Such a sensor is frequently referred to as an oxygen sensor, since it is principally responsive to oxygen. However, I recognize that such a sensor should also be responsive to the oxides of nitrogen as well, particularly nitric oxide. Otherwise the sensor will not register a true exhaust gas stoichiometry. The sensor may be indicating stoichiometry, when the exhaust gases are in fact lean due to increased NO$_x$ content. It was not previously recognized whether such exhaust gas sensors were responsive to NO$_x$, or whether NO$_x$ response was even significant.

The automotive exhaust gas sensor currently of greatest interest is a galvanic cell having a zirconia solid electrolyte body. The zirconia body has a reference electrode and an exhaust gas electrode. The exhaust gas electrode is a platinum film, usually with a porous overcoat to not only protect the platinum film but to enhance obtaining exhaust gas equilibrium at the platinum electrode. It has been previously proposed to make the porous overcoat of a catalytic ceramic and/or include a catalyst such as platinum in the coating to further enhance obtaining chemical equilibrium at the platinum electrode. It was expected that if chemical equilibrium were reached, true stoichiometry would be measurable. I have now found that such a sensor is not necessarily responsive to oxides of nitrogen. If so, it may be indicating stoichiometry when the exhaust gases are in fact not balanced. However, I have also found that nitrogen oxide responsiveness is obtained, without losing oxygen responsiveness, by adding rhodium to the exhaust gas electrode system. It may even be desirable to include rhodium at the exhaust electrode to insure high NO$_x$ sensitivity for longer periods of time.

OBJECTS AND SUMMARY OF THE INVENTION

It is, therefore, an object of this invention to provide enhanced oxides of nitrogen sensitivity in a solid electrolyte oxygen sensor for determining exhaust gas stoichiometry.

The invention comprehends an oxygen responsive stoichiometric exhaust gas sensor having a solid electrolyte and an electrode for exposure to an exhaust gas. The exhaust gas electrode contains both a reducing catalyst in addition to an oxidizing catalyst for enhanced oxides of nitrogen sensitivity. In a preferred example, the sensor has a zirconia electrolyte body with an RF sputtered platinum exhaust gas electrode. The electrode is overcoated with porous gamma alumina that is impregnated with rhodium.

BRIEF DESCRIPTION OF THE DRAWING

Other objects, features and advantages of the invention will become more apparent from the following description of preferred examples thereof and from the drawing, in which.

Figure 1:
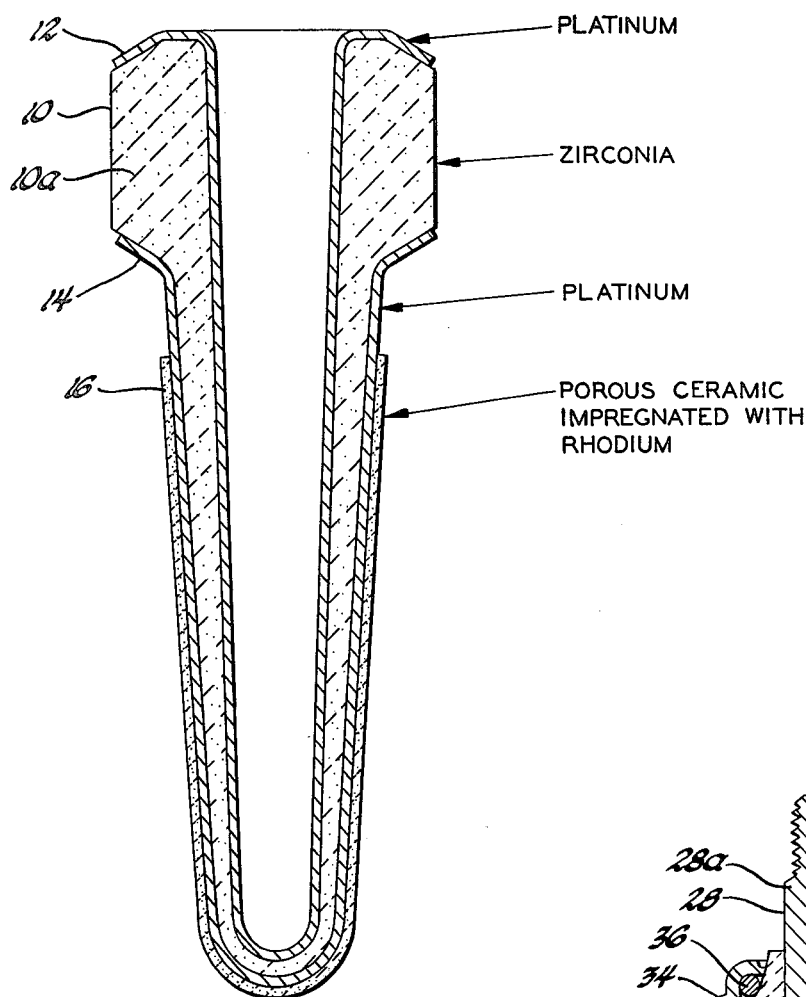
FIG. 1 shows an enlarged sectional view of a solid electrolyte galvanic cell formed in accordance with this invention.

DESCRIPTION OF THE PREFERRED EMBODIMENTS:

FIG. 1 shows a flanged, cup-like solid electrolyte member 10. The solid electrolyte is a ceramic material having oxygen ion vacancies in its crystal lattice that are mobile at an elevated temperature. A substance having a fluorite-type crystal lattice, such as cubic zirconia, thoria, or the like, can be used. If of zirconia, the solid electrolyte can be partially or fully stabilized in the cubic crystal structure by additions of 5-8 mole percent Y$_2$O$_3$, or 8-15 mole percent calcium oxide.

An inner porous platinum coating 12 covers the cup interior. It extends up to and around the upper edge of cup flange 10a. This coating 12 serves as a reference electrode when exposed to air. However, it can be of any material which, upon exposure to air or an oxide mixture, will provide a reference potential. For example, it can be of platinum paste fired in the normal and accepted manner. However, it might also be of gold, silver or palladium. Moreover, it could be nickel and the cup filled with nickel oxide to provide a reference potential. Many variations on the reference electrode have been proposed. This invention is not dependent on any of them for operability. They are as useful with the exhaust electrode of this invention as they would be with any other oxygen sensor exhaust electrode.

A thin porous platinum coating 14 entirely covers the outer surface of electrolyte body 10 up to and including the lower portion of cup flange 10a. Platinum coating 14 serves as an exhaust electrode. It is applied by RF sputtering. However, DC sputtering may also be useful, as well as chemical vapor deposition, evaporation, or thermal decomposition techniques. Platinum electrode 14 has a thickness of about 0.4 micrometer up to about 1-1.5 micrometers to increase its adhesion and/or pore size. Pore size of electrode 14 may vary from so small in diameter as to not be measurable up to about or somewhat greater than the thickness of the coating. A porous ceramic overcoat 16 substantially entirely covers electrode 14 below flange 10a. With platinum coating 14, overcoat 16 provides an exhaust electrode system. Overcoat 16 is of a calcined refractory consisting essentially of about 5 to 70 weight percent fumed alumina and the balance active alumina formed from alpha alumina monohydrate or pseudobohemite, as disclosed in U.S. Pat. No. 4,116,883, entitled "Catalyst Support Coating Slurry and Coatings", filed by J. F. Rhodes on Feb. 26, 1975, and assigned to the assignee of this patent application. Other catalytic coatings are disclosed in U.S. Pat. No. 3,565,830 Keith. U.S. Pat. Nos. 3,978,006 Topp et al and 4,021,326 Pollner et al describe analogous electrochemical sensing cells, electrodes, electrode overcoats and methods of forming them.

Porous protective overcoat 16 is impregnated with rhodium. In other words, its pores (not shown) are coated with rhodium. In a preferred form, the rhodium coating is not continuous. Instead, it is of finely divided rhodium particles, produced in situ by chemical deposition techniques. For example, after overcoat 16 is formed, the rhodium coating can be produced by dipping the electrolyte cup in an aqueous solution containing about 4% by weight rhodium trichloride, and then heating to a temperature of about 115° C. for a few hours, followed by calcining at a temperature of about 550° C. for about one hour in a nonoxidizing atmosphere. This thermally decomposes the rhodium salt into a fine dispersion of rhodium particles throughout the pores in coating 16. Rhodium particles less than about 0.15 micrometer in maximum dimension are desirable, and preferably less than about 0.01 micrometer in maximum dimension. It is expected the best results would be obtained with rhodium particles that are colloidal or subcolloidal in size, wherein each particle is in essence a unitary crystal. The manner in which the rhodium dispersion in the porous ceramic overcoat is formed is not critical so long as rhodium is effectively exposed in the coating. It may be useful to include platinum particles in coating 16 as it is formed, rather than subsequently impregnating it. Also, it may be preferred to simply dip the overcoated electrolyte body in an aqueous mixture containing 1–3 percent by weight colloidal particles of rhodium, and then heat the body to a temperature of approximately 200°–500° C. to enhance adhesion of the particles to the ceramic overcoat.

In retrospect, I believe that the rhodium provides enhanced $NO_x$ sensitivity by providing a more complete chemical equilibrium at the exhaust electrode. I believe that a more complete catalysis to equilibrium is attained because it is known that rhodium is primarily a reducing catalyst and that platinum is primarily an oxidizing catalyst. It might thus be useful to make the platinum electrode of a platinum-rhodium mixture or alloy, and/or include a platinum-rhodium mixture or alloy in the protective overcoat. In the alternative it may even be desirable to include a rhodium layer over or under the platinum layer, with or without rhodium in the overcoat 16. Further, it may be desirable to substitute palladium for platinum in the electrode to obtain a more effective carbon monoxide catalyst, even though the palladium may be more subject to poisoning. In any event, electrode 14 should promote true equilibrium of all species, including oxides of nitrogen. This is most important for an exhaust gas sensor which is intended to operate substantially only at exhaust gas stoichiometry in combination with a three-way catalytic converter downstream in exhaust gas flow.

Figure 2:
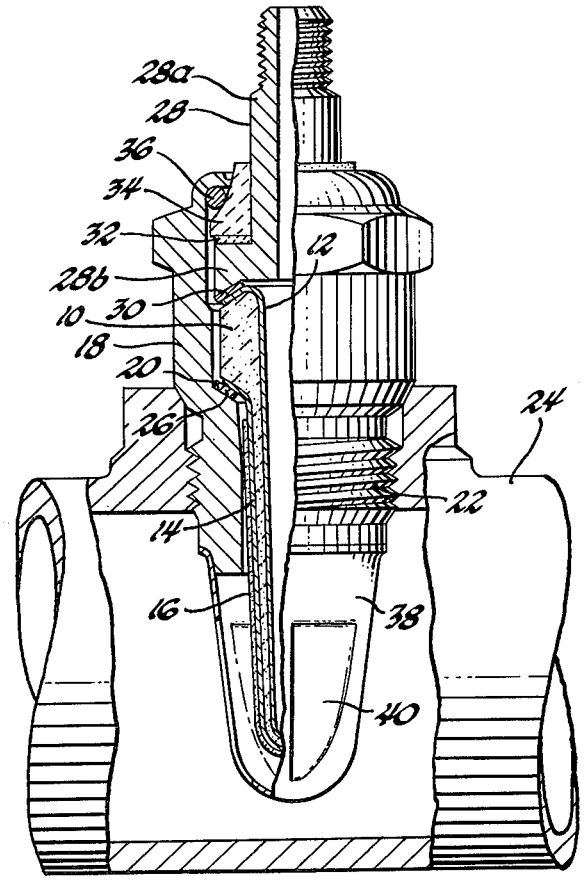
FIG. 2 shows an elevational view in partial section of the FIG. 1 cell incorporated in a housing assembly.

FIG. 2 shows the assembled sensor. Electrolyte body 10, after coated as described in connection with FIG. 1, is coaxially disposed in a vertically oriented tubular metal shell 18. The interior of metal shell 18 has a larger diameter in its upper end than its lower end, forming an inner circumferential shoulder 20. The lower end of shell 18 is externally threaded at 22 to mount the sensor in an exhaust pipe 24.

The coated electrolyte body of FIG. 1 forms a galvanic cell. The cell is coaxially supported in metal shell 18. Electrolyte flange 10 seats on a lower soft metal seating ring 26, which is in turn seated on shell shoulder 20. Sealing ring 26 contacts both the cell outer electrode 14 and the metal shell 18, whereby exhaust pipe 24 is in low resistance electrical communication with outer electrode 14.

Above the galvanic cell is a coaxial terminal member 28 for inner electrode 12. Terminal member 28 has a tubular axial portion 28a and a circumferential flange 28b at its bottom end. The lower surface of flange 28b seats on a soft metal sealing ring 30 which in turn seats on the supper edge of the electrolyte body 10, where inner electrode 12 extends therearound. Terminal member 28 is thus in low resistance electrical communication with inner electrode 12. A flat mica washer 32 and an alumina ring 34 are successively coaxially nested around terminal tubular portion 28a above terminal flange 28b. The alumina ring 34 has an upward decreasing taper on its outer surface around which is an annular metal gasket 36. The upper end of metal shell 18 is crimped or rolled over metal gasket 36 to clamp the alumina ring, mica washer, terminal flange 28b, soft metal sealing rings 26 and 30 and the sensor cell against shell shoulder 20. They are coaxially disposed in metal shell 18, whereby the enlarged inner diameter of the shell and the alumina ring 34 permit terminal member 28 to be electrically isolated from shell 18. Accordingly, a discrete terminal for inner electrode 12 is provided. Terminal member tubular portion 28a is hollow to allow ambient air to contact the cell inner electrode 12.

A coaxial cup-like metal shield 38 is provided over the lower end of the sensor cell that projects below metal shell 18. The shield 38 has a plurality of louvers 40 therein to permit exhaust gases in exhaust pipe 24 to contact the outer electrode 14 on the cell through the porous protective overcoat 16.

It is to be recognized that the electrolyte body shape and the specific sensor assembly illustrated in FIGS. 1 and 2 is only one of many such shapes and assemblies which could be used. The invention is not limited to such shapes and assemblies. For example, this invention could be used in the sensor assembly shown and described in United States patent application Ser. No. 892,643, entitled "Heated Solid Electrolyte Oxygen Sensor", filed Apr. 3, 1978, by M. P. Murphy and G. W. Hillebrand and assigned to the assignee of this invention.

The embodiments of the invention in which an exclusive property or privilege is claimed are defined as follows:

1. In a solid electrolyte exhaust gas oxygen responsive sensor having a catalytic exhaust gas electrode for producing chemical equilibrium of oxidizable exhaust gas constituents and a porous protective coating on said electrode, the improvement wherein rhodium is included in said protective coating to attain a more complete chemical equilibrium and enhance sensor response to oxides of nitrogen.

2. In a solid electrolyte exhaust gas oxygen responsive sensor having a platinum exhaust gas electrode and a porous ceramic coating on that electrode, the improvement wherein rhodium is included in the protective coating effective to make sensor output voltage responsive to oxides of nitrogen, as well as oxygen, in the exhaust gas.

3. In a zirconia electrolyte exhaust gas oxygen responsive sensor having a platinum exhaust gas electrode and a substantially gamma alumina porous overcoat on the platinum electrode, the improvement wherein the gamma alumina overcoat is permeated with rhodium, effective to make sensor output voltage not only responsive to oxygen in the exhaust gas but also to nitric oxide, whereby exhaust gas stoichiometry is more accurately represented.

* * * * *